United States Patent
Minakawa et al.

(10) Patent No.: US 10,317,203 B2
(45) Date of Patent: Jun. 11, 2019

(54) DIMENSION MEASURING APPARATUS AND COMPUTER READABLE MEDIUM

(71) Applicant: HITACHI HIGH-TECHNOLOGIES CORPORATION, Tokyo (JP)

(72) Inventors: Tsuyoshi Minakawa, Tokyo (JP); Yasutaka Toyoda, Tokyo (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 1102 days.

(21) Appl. No.: 13/789,619

(22) Filed: Mar. 7, 2013

(65) Prior Publication Data

US 2013/0325397 A1 Dec. 5, 2013

(30) Foreign Application Priority Data

May 31, 2012 (JP) ................................ 2012-123886

(51) Int. Cl.
  *G01B 21/20* (2006.01)
  *G01N 21/956* (2006.01)

(52) U.S. Cl.
  CPC ....... *G01B 21/20* (2013.01); *G01N 21/95607* (2013.01); *G01B 2210/56* (2013.01)

(58) Field of Classification Search
  CPC ................ G01B 21/20; G01B 2210/56; G01N 21/95607
  See application file for complete search history.

(56) References Cited

U.S. PATENT DOCUMENTS

| | | | |
|---|---|---|---|
| 7,702,157 B2 | 4/2010 | Mitsui | |
| 8,019,161 B2 | 9/2011 | Morokuma et al. | |
| 8,045,785 B2 | 10/2011 | Kitamura et al. | |
| 9,165,214 B2 | 10/2015 | Abe et al. | |
| 2004/0205688 A1* | 10/2004 | Pierrat | G06F 17/5068 716/53 |
| 2007/0221842 A1* | 9/2007 | Morokuma | G01N 23/2251 250/307 |
| 2008/0033699 A1* | 2/2008 | Hioki | G05B 19/4103 703/1 |

FOREIGN PATENT DOCUMENTS

| | | |
|---|---|---|
| JP | 2004-185019 A | 7/2004 |
| JP | 2006-275952 A | 10/2006 |
| JP | 2012-052810 A | 3/2012 |

* cited by examiner

*Primary Examiner* — Alexander Satanovsky
(74) *Attorney, Agent, or Firm* — McDermott, Will & Emery LLP

(57) ABSTRACT

A dimension measuring apparatus for measuring a dimension between a first data contour which is an evaluation reference of a pattern to be evaluated and a second data contour which is the pattern to be evaluated generates first correspondence information between a point on the first data contour and a point on the second data contour, determines consistency of a correspondence included in the first correspondence information, corrects an inconsistent correspondence, and generates second correspondence information, when associating a point on the first contour data and a point on the second contour data with each other.

9 Claims, 11 Drawing Sheets

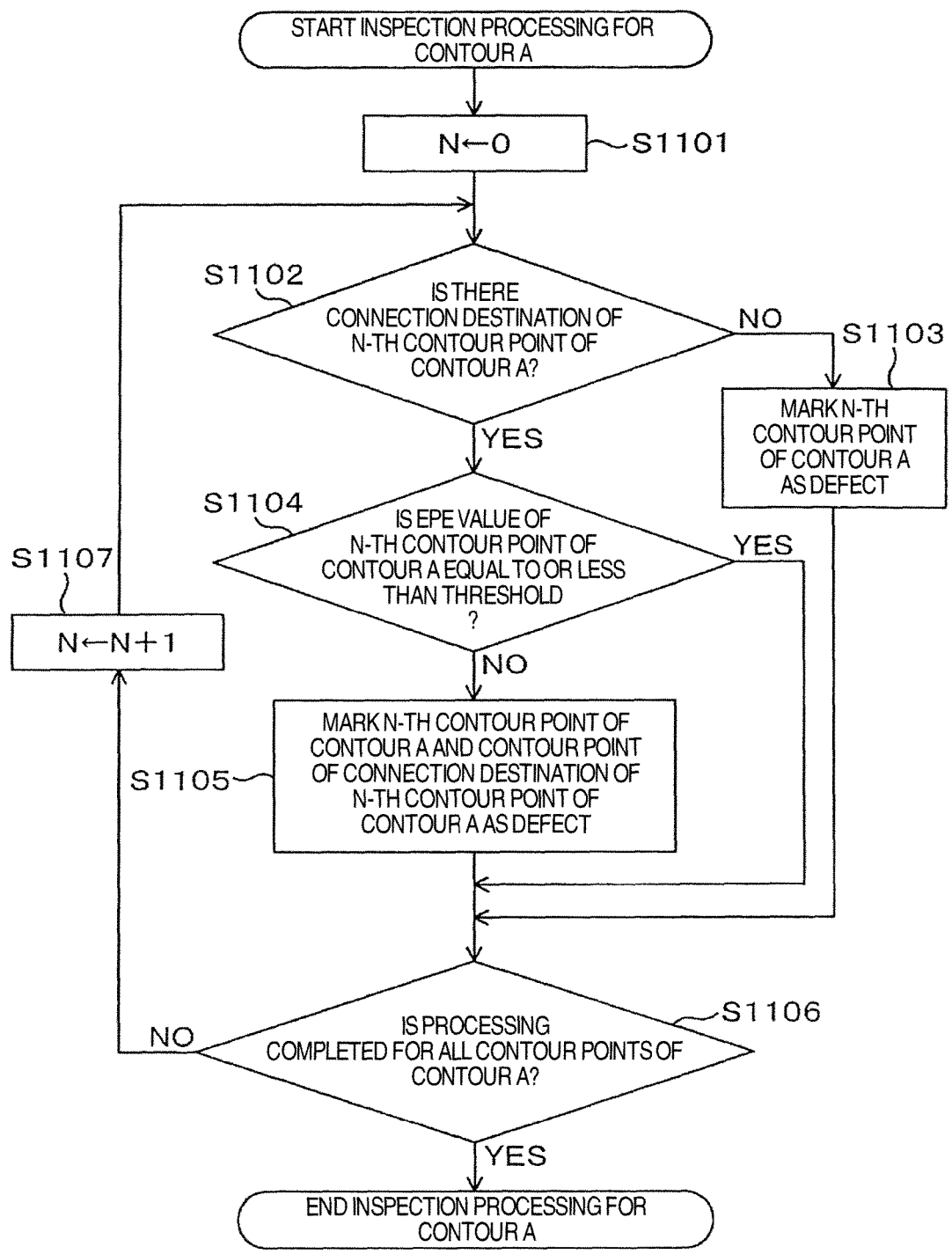

DIMENSION MEASURING APPARATUS AND COMPUTER READABLE MEDIUM

BACKGROUND OF THE INVENTION

The present invention relates to an apparatus for measuring a dimension between a reference pattern and a pattern to be evaluated and a computer program for causing a computer to perform the measurement, and more particularly to a dimension measuring apparatus for measuring a dimension between corresponding points in a reference pattern and in a pattern to be evaluated and a computer program.

As the process rule for semiconductors evolves and a finer pattern is transcribed onto a wafer, an inspection utilizing design data becomes more useful for detection of a systematic defect caused by a design flaw of a mask or the like and for better dimension management. This is attributed to the increased importance of a measure against a systematic defect because, in addition that margins in setting of parameters for design and transfer of a mask are decreased so that a systematic defect tends to be generated, unlike a random defect, a systematic defect can be efficiently dealt with by identifying a cause of generation and taking a remedy.

A systematic defect, which is generated in the similar manner in all dies, cannot be detected by a conventional inspection in which dies are compared with each other, and it is desirable to be evaluated by an inspection by comparison to the design data or by dimension management using the design data. In addition, as for dimension measurement, dimension measurement of only one-dimensional features is getting insufficient and an increasing need has arisen for evaluation of two-dimensional shapes.

Against such a background, as examples of inspection technologies utilizing design data, there are those disclosed in JP-A-2006-275952 and JP-A-2004-185019.

In JP-A-2006-275952, disclosed is a technology in which a contour of a reference pattern and a contour of an inspection pattern are compared with each other and inspected using distance transform images. More specifically, a distance transform image generated from a contour of a reference pattern is used to obtain a distance from each of the points on a contour of an inspection pattern to the nearest point on the contour of the reference pattern and, using the obtained distance, the inspection pattern is evaluated.

In JP-A-2004-185019, disclosed is a technology in which, by introducing a concept of an "edge" that is defined on a pixel basis and has a start point with sub-pixel accuracy and a direction of a contour at the pixel, a correspondence between a point on a contour of a reference pattern and a point on a contour of an inspection pattern is obtained while not only a distance but also a direction is considered so that the contour of the reference pattern and the contour of the inspection pattern are compared with each other and inspected using the obtained correspondence.

SUMMARY OF THE INVENTION

As the process rule evolves and the pattern dimension becomes smaller, the density of patterns formed on a wafer increases and the number of points requiring inspection or the like increases. Therefore, from the viewpoint of suppressing dimension measurement time, there is an increasing need for capturing an image in a relatively large field of view (FOV) with respect to a dimension of a pattern to be measured (capturing an image at a low magnification) and selecting measuring points at a higher magnification.

In an inspection by comparing a contour of a reference pattern and a contour of an inspection pattern with each other or the like, correct correspondence between points on the contour of the reference pattern and points on the contour of the inspection pattern is important, when the correspondence is made using distances between the points as in the idea disclosed in JP-A-2006-275952, the distance to a neighboring pattern becomes smaller as the density of formed patterns becomes higher and, in some cases, with a small pattern deformation a mistake in corresponding points can occur.

Also, in an image captured at low magnification, the white bands tend to become unclear in an area of dense patterns and there are possibilities that extraction of a contour line of a pattern is omitted or a part that is not a contour line of a pattern is extracted as a contour line, leading to an increase in the possibility of mistakes in corresponding points due to them.

Besides, a pattern deformation is allowed within the range in which electric properties are guaranteed even for those considered to be "good" in patterns transcribed onto a wafer and, in fact, not a few deformations of patterns due to differences in exposure conditions or the like occur. Such deformations can cause mistakes in corresponding points. In addition. when there is actually a defect, a mistake in corresponding points tends to happen easily due to a shape deformation or the like in a defective part.

A study conducted by the inventors revealed that a mistake in corresponding points described above is originated in adopting the correspondence obtained only from local information (for example, distances between points) and by not considering with regard to "correspondence consistency" based on the surrounding conditions. Therefore, even in a case where the correspondence is obtained considering not only the distance but also the direction as in the technology disclosed in JP-A-2004-185019, it still occurs.

Hereinafter, a dimension measuring apparatus and a computer program with which it is aimed to suppress a mistake in corresponding points between a reference pattern and a pattern to be evaluated are proposed.

As one aspect to achieve the above objective, there are proposed a dimension measuring apparatus for measuring a dimension between a first data contour which is an evaluation reference of a pattern to be evaluated and a second data contour which is the pattern to be evaluated including an operation device which associates a point on the first data contour and a point on the second contour data contour with each other, wherein the operation device generates first correspondence information between a point on the first contour data contour and a point on the second data contour, determines consistency of correspondences included in the first correspondence information, corrects an inconsistent correspondence, and generates second correspondence information and a computer program that causes a computer to perform the processings described above.

Also, there are proposed a dimension measuring apparatus for measuring a dimension between a first data contour which is an evaluation reference of a pattern to be evaluated and a second data contour which is the pattern to be evaluated including an operation device which associates a point on the first contour data contour and a point on the second data contour with each other, wherein the operation device obtains a second point on one data contour out of the first and second data contour, each of which is divided into a plurality of segments configuring a pattern, the second point corresponding to a first point on an other data contour, obtains a third point on the other contour data contour that corresponds to the second point, and judges whether a segment to which the first point belongs and a segment to which the third point belongs are the same or not, and a computer program that causes a computer to perform the processings described above.

According to the configuration described above, a mistake in corresponding points between a reference pattern and a pattern to be evaluated can be suppressed.

Other objects, features, and advantages of the invention will become apparent from the following description of the embodiments of the invention taken in conjunction with the accompanying drawings.

BRIEF DESCRIPTION OF THE DRAWINGS

FIG. 3A is a diagram showing a state prior to the segment resolving processing and FIG. 3B is a diagram showing a state after the segment resolving processing;

FIG. 4A is a diagram showing a correspondence from a contour of a reference pattern to a contour of an inspection pattern and FIG. 4B is a diagram showing a correspondence from the contour of the inspection pattern to the contour of the reference pattern;

FIG. 9A is a diagram showing a correspondence from the contour of the reference pattern to the contour of the inspection pattern and FIG. 9B is a diagram showing a correspondence from the contour of the inspection pattern to the contour of the reference pattern;

FIG. 10A is a diagram showing a state in which an incorrect correspondence part is detected in and excluded from a correspondence from the contour of the reference pattern to the contour of the inspection pattern and FIG. 10B is a diagram showing a state in which the incorrect correspondence is corrected in the correspondence from the contour of the reference pattern to the contour of the inspection pattern;

FIG. 11 is a flowchart showing an operation of an inspection unit eluded in the operation device of the dimension measuring apparatus;

DESCRIPTION OF THE EMBODIMENTS

In the embodiments described below, described are a dimension measuring apparatus with which it is intended to improve reliability of inspection results in inspection by comparison of a contour of a reference pattern and a contour of an inspection pattern primarily by providing a technology for reducing an incorrect correspondence between points on the contour of the reference pattern and points on the contour of the inspection pattern and a computer program which causes a computer to perform the processing described above. Incidentally, for the sake of simplicity of explanation, in the description of the present embodiments, dimension measurement, defect inspection, and the like are represented collectively as an "inspection".

In order to achieve the above objective, in the embodiments described below, a description is given primarily on a pattern inspection device for comparing a first contour which is a contour of a reference pattern becoming an evaluation reference for a pattern to be inspected and a second contour which is a contour extracted from an image created by imaging the pattern to be inspected, which includes a correspondence generation unit that generates first correspondence information by associating points on the first contour and points on the second contour with each other, a correspondence correction unit that generates second correspondence information by determining consistency of correspondences included in the first correspondence information and correcting an inconsistent correspondence, and an inspection unit that carries out inspection using the second correspondence information, and a computer program.

According to the configuration described above, by adopting a configuration in which consistency is judged based on the surrounding, conditions with regard to correspondences obtained from local information, and a correspondence which is estimated to be inconsistent is corrected and used in inspection, the frequency can be reduced at which an incorrect correspondence between a point on a contour of a reference pattern and a point on a contour of an inspection pattern is used in an inspection, thus improving reliability of the inspection result.

First Embodiment

Figure 1:
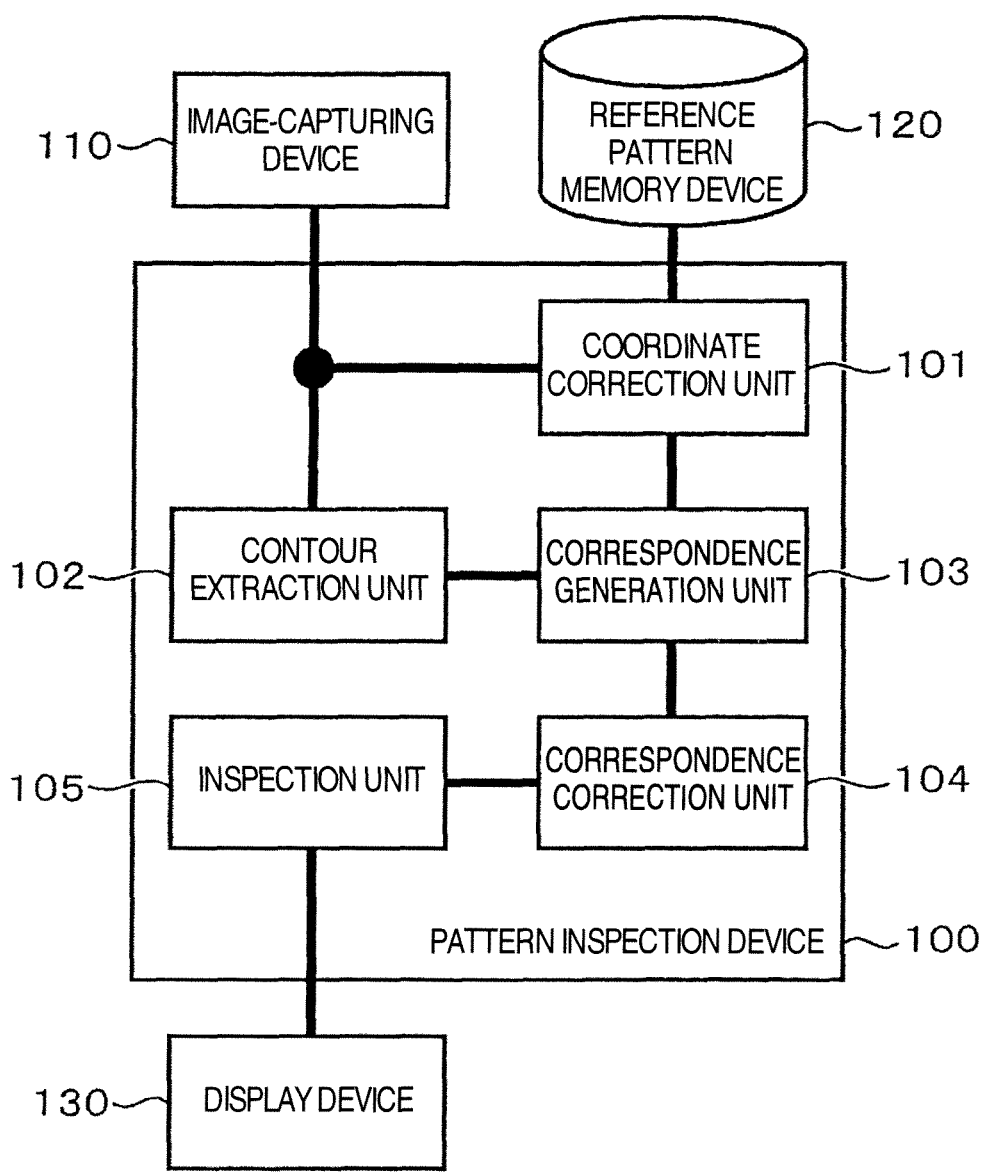
FIG. 1 is a diagram explaining a configuration of a dimension measuring apparatus.

A first embodiment is described below with reference to FIG. 1 to FIG. 11. As shown in FIG. 1, a pattern inspection device 100 reads an inspection image (a pattern data to be evaluated) and a reference pattern data, inspects the inspection image by comparing their contours with each other (for example, measuring dimensions between corresponding points), and outputs an inspection result.

An image-capturing device 110 captures a semiconductor pattern formed on a wafer, and supplies it to the pattern inspection device as an inspection image together with parameters at image-capturing; for example, it is a scanning electron microscope.

A reference pattern memory device 120 stores reference patterns each being an evaluation reference of a pattern to be inspected; for example, it is a hard disk. Incidentally, in this embodiment, a curve that forms an outer shape of an exposure pattern obtained with a lithography simulator is approximated with a polygon and used as a reference pattern. A display device 130 is a display that displays an inspection result output by the pattern inspection device

[Configuration of Pattern Inspection Device 100]

As shown in FIG. 1, the pattern inspection device 100 comprises a coordinate correction unit 101, a contour extraction unit 102, a correspondence generation unit 103, a correspondence correction unit 104, and an inspection unit 105.

The coordinate correction unit 101 obtains a relation between the coordinate system of the inspection image and the coordinate system of the reference pattern using parameters at image-capturing, an inspection image supplied from the image-capturing device 110, and a reference pattern supplied from the reference pattern memory device 120, cuts out a part necessary for inspection out of the reference pattern, converts into a representation in the coordinate system of the inspection image, and supplies to the correspondence generation unit 103, This processing may be performed using a known technique; for example, the method disclosed in JP-A-2004-185019 or a method such as the template matching may be used.

The contour extraction unit 102 extracts a contour of an inspection pattern from the inspection image supplied from the image-capturing device 110 and supplies to the correspondence generation unit 103. Extraction of the contour of the inspection pattern may be performed using a known technology. For example, the method called the Canny method, the method disclosed in JP-A-2004-185019, or the like may be used. It is noted that thinning processing would have been performed in advance on the contour extracted by the contour extraction unit 102 using a known technology.

The correspondence generation unit 103 associates the contour (a set of polygons) of the reference pattern supplied from the coordinate correction unit 101 and the contour of the inspection pattern extracted in the contour extraction unit 102 with each other to generate the correspondence information and supplies it together with the contour information on the reference pattern and the contour information on the inspection pattern to the correspondence correction unit 104. The operation of the correspondence generation unit 103 is described later in detail (see FIG. 2). Incidentally, the "contour information" refers to the information on a contour for which processing up to contour point setting described later (see FIG. 2) is performed, that is a set of the contour point information and their connection information. Here, as for the contour point information, two-dimensional coordinates which indicate positions in the inspection image where the contour points are present are stored. Besides, the correspondence information comprises, for each of all contour points, identifiers of the corresponding contour points (described later: see FIG. 2), flags indicating whether they are incorrect correspondences or not (described later: see FIG. 6), and flags indicating whether they are defects or not (described later: see FIG. 11).

The correspondence correction unit 104 detects a correspondence which is estimated to be inconsistent as an incorrect correspondence out of correspondences included in the correspondence information supplied from the correspondence generation unit 103 in light of the contour information on the reference pattern, the contour information on the inspection pattern, and other correspondence information, and corrects it to be consistent, then, it supplies the correspondences with correction along with the contour information on the reference pattern and the contour information on the inspection pattern to the inspection unit 105. The operation of the correspondence correction unit 104 is described later in detail (see FIG. 5).

The inspection unit 105 inspects the inspection pattern using the correspondence information after correction supplied from the correspondence correction unit 104, the contour information on the reference pattern, and the contour information on the inspection pattern, and outputs inspection results to the display device 130. The operation of the inspection unit 105 is described later in detail (see FIG. 11).

[Operation of Correspondence Generation Unit 103 in Pattern Inspection Device 100]

Description is given next on the operation of the correspondence generation unit 103 with reference to FIG. 2 to FIG. 4B.

Figure 2:
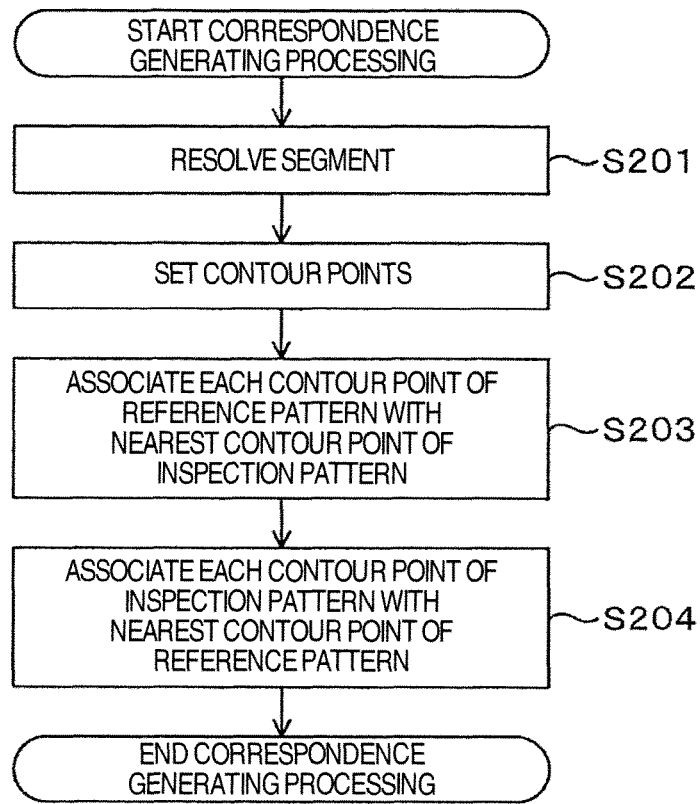
FIG. 2 is a flowchart showing an operation of a correspondence generation unit included in an operation device of the dimension measuring apparatus.

As shown in the flowchart in FIG. 2, the correspondence generation unit 103 performs segment resolving processing in Step S201. The purpose of the segment resolving processing is to eliminate branches in a contour, that is to resolve a contour into "closed paths" and "non-branching lines". In the following part of the description, both "closed paths" and "non-branching lines" are called "segments".

Figure 3A:
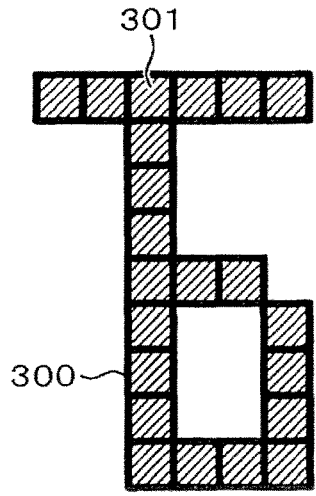
FIG. 3A and FIG. 3B are diagrams for explaining an operation in segment resolving processing that is among the operations of the correspondence generation unit included in the operation device of the dimension measuring apparatus.
Figure 3B:
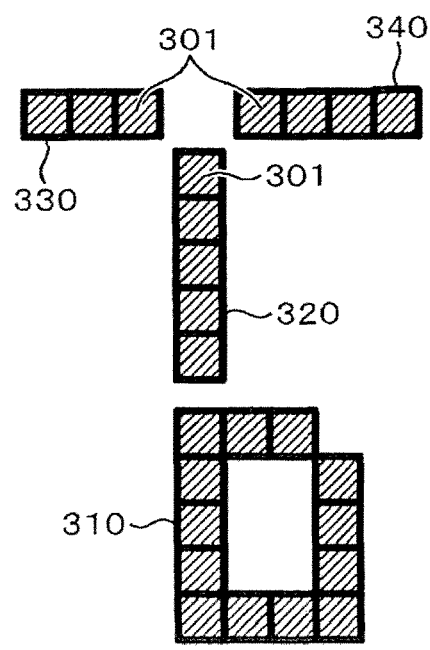

The content of the segment resolving processing is described with reference to FIG. 3A and FIG. 3B. FIG. 3A shows a state before segment resolving. When segment resolving is performed on a contour 300 in FIG. 3A, it is resolved into a segment 310, a segment 320, a segment 330, and a segment 340 shown in FIG. 3B. Here, the segment 310 is a closed path, and the segment 320, segment 330, and segment 340 are non-branching lines. At this time, a branching point is shared by the segments related to the branching point. For example, a branching point 301 is shared by the segment 320, the segment 330, and the segment 340, as an end point (a start point or a finish point).

The segment resolving processing may be performed using a known technique, and, besides, because a contour of a reference pattern does not usually contain branching, the segment resolving processing is needed to be performed only for a contour of an inspection pattern. Incidentally, if there is a possibility that a contour of a reference pattern may have a branch, the segment resolving processing is performed also for the contour of the reference pattern. As for a data structure of each segment, for example, a set of the number of registered points and an array in which the coordinates of the registered points are arranged following the order from the start point to the finish point may be used.

In Step S202, the correspondence generation unit 103 performs contour point setting processing. The contour point setting processing is processing in which, for each segment with one end as a start point and the other as a finish point, a path from the start point o the finish point is divided into equally-spaced sections along the shape of the segment and "contour points", which are used for calculation in comparing processing between contours, are arranged at the start point, the finish point, and the boundary positions of respective sections. As for a maximum value of lengths of the sections, that is a maximum interval between contour points, an appropriate value is set in advance as a design value according to required accuracy.

When the segment length of a segment, namely the route from the start point to the finish point is "L" and the maximum interval between contour points is "S", for example, a number obtained by dividing L by S and rounding up to the nearest integer with adding may be the number of the contour points on the segment. In terms of the segment length, the lengths of the polygonal lines from the start point to the finish point may be added up. For a segment that forms a closed path, the processing is performed with an appropriate point of the segment as the start point and the finish point.

Figure 4A:
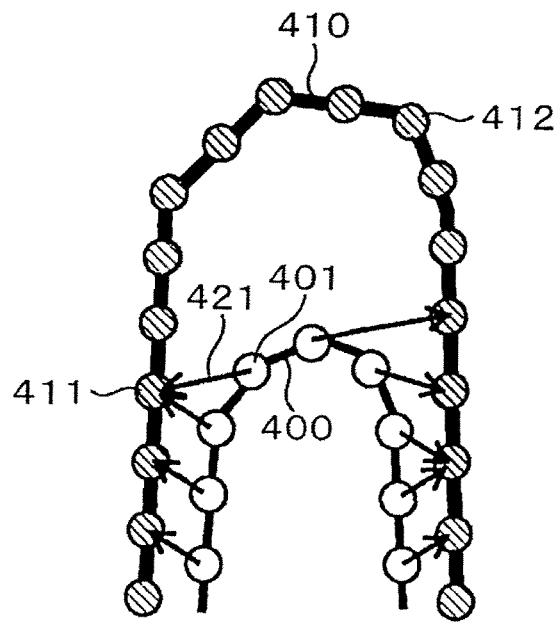
FIG. 4A and FIG. 4B are diagrams explaining a correspondence between two contours.

Next, in Step S203, the correspondence generation unit 103 associates each contour point of the reference pattern with the nearest contour point of the inspection pattern The results of the association in Step S203 are, for example, shown in FIG. 4A. In FIG. 4A, a contour point 401 existing on a contour 400 of the reference pattern is associated with a contour point 411 existing on a contour 410 of the inspection pattern that is the nearest contour point of the inspection pattern. Search for the nearest contour point may be performed with a known technology, such as a method by brute-force search, a method using a Voronoi diagram, or a method using a distance transform image, or using a combination of those methods.

Similarly, in Step S204, the correspondence generation unit 103 associates each contour point of the inspection pattern with the nearest contour point of the reference pattern. The results of the association in Step S204 is as shown in FIG. 4B, for example.

Figure 4B:
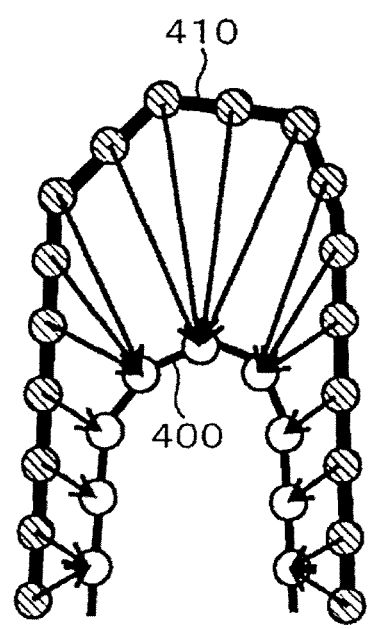

Here, the correspondences generated in Step S203 and Step S204 are correspondences with directions as shown in FIG. 4A and FIG. 4B; in general, the results of the associations from the contour 400 of the reference pattern to the contour 410 of the inspection pattern shown in FIG. 4A are different from the results of the associations from the contour of the inspection pattern to the contour of the reference pattern shown in FIG. 4B. Correspondences with directions allow point-to-point associating processing to be simple distance-based processing.

Also, in the correspondences from the contour 400 of the reference pattern to the contour 410 of the inspection pattern, each of all contour points on the contour of the reference pattern is associated with any one of the contour points on the contour of the inspection pattern, on the other hand, as shown with a contour point 412 on the contour 410 of the inspection pattern, there is no guarantee that each of all contour points on the contour of the inspection pattern is associated with any one of the contour points on the contour of the reference pattern. Similarly, in the correspondences from the contour of the inspection pattern to the contour of the reference pattern, while each of all contour points on the contour of the inspection pattern is associated with any one of the contour points on the contour of the reference pattern, there is no guarantee that each of all contour points on the contour of the reference pattern is associated with any one of the contour points on the contour of the inspection pattern.

Hereinafter, a relation such as the one between the contour point 401 and the contour point 411 in FIG. 4A is defined as "the connection destination of the contour point 401 is the contour point 411" and a directed line segment 421 from the contour point 401 to the contour point 411 is called a "connection line segment corresponding to the contour point 401". At the time when Step S203 and Step S204 are completed, just one connection line segment corresponds to each contour point.

As shown in FIG. 4, in a part where a separation between the reference pattern and the inspection pattern is large, there is a long one among the connection line segments corresponding to the contour points of the reference pattern or the connection line segments corresponding to the contour points of the inspection pattern. In the present embodiment, this property is used in inspection performed in the inspection unit 105. The operation of the inspection unit 105 is described later in detail (see FIG. 11).

[Operation of Correspondence Correction Unit 104 in Pattern Inspection Device 100]

Figure 5:
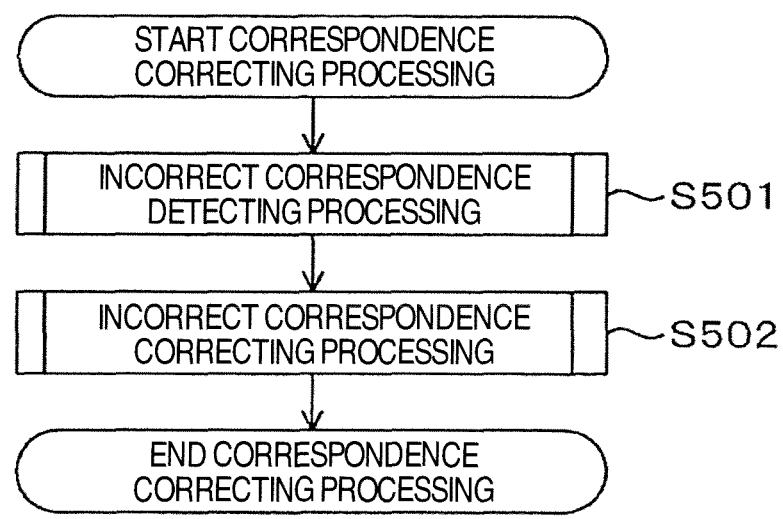
FIG. 5 is a flowchart showing an operation of a correspondence correction unit included in the operation device of the dimension measuring apparatus.

Next, a description is given on the processing of the correspondence correction unit 104 with reference to FIG. 5. As shown in the flowchart in FIG. 5, the correspondence correction unit 104 performs the incorrect correspondence detecting processing in Step S501. This processing is described later in detail (see FIG. 6).

Next, in Step S502, the correspondence correction unit 104 performs the incorrect correspondence correcting processing. Incidentally, this processing is described later in detail (see FIG. 8). After the incorrect correspondence correcting processing in Step S502 is completed, the correspondence correction unit terminates the correspondence correcting processing.

[Incorrect Correspondence Detecting Processing]

Figure 6:
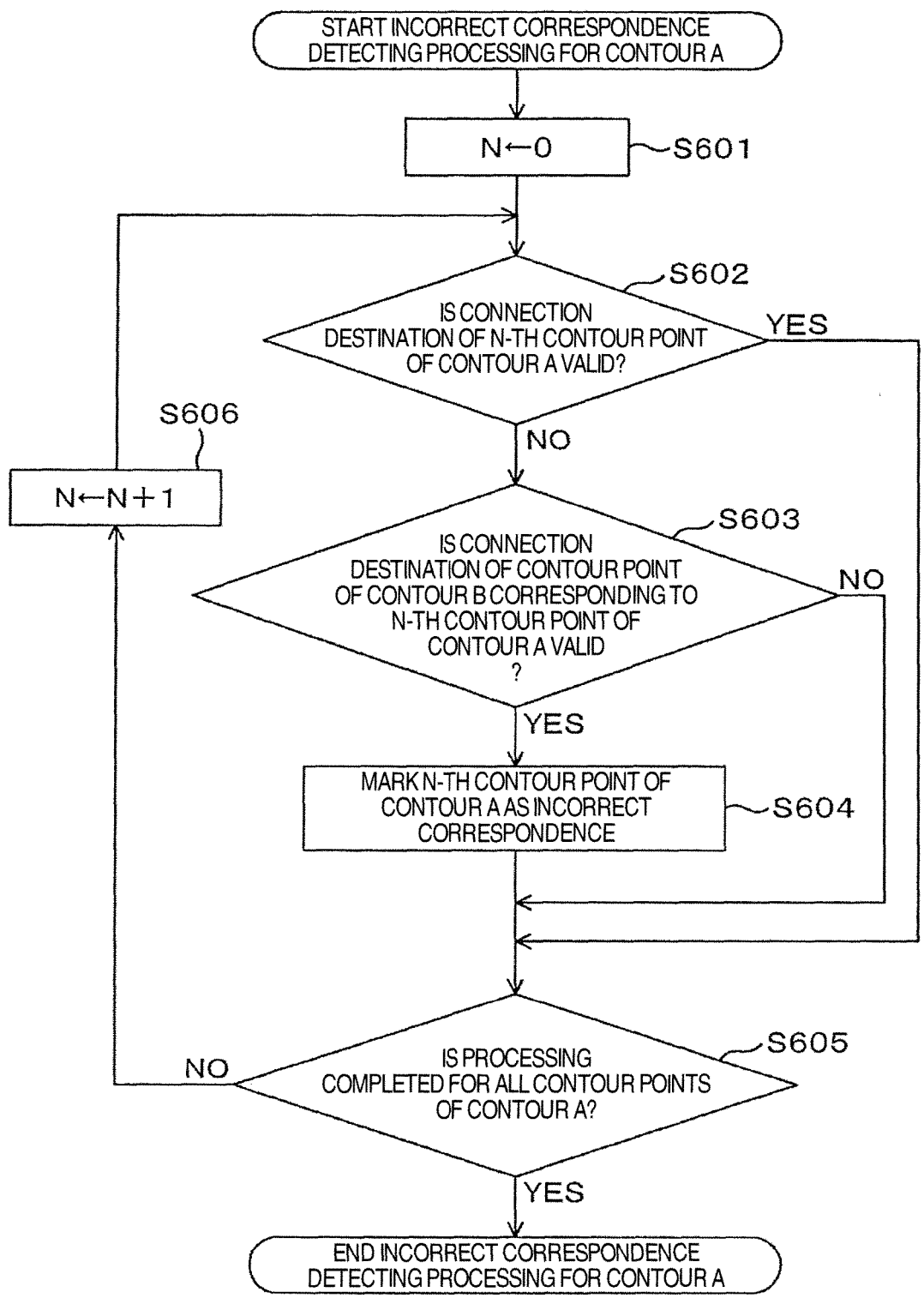
FIG. 6 is a flowchart explaining an operation in incorrect correspondence detecting processing that is among the operations of the correspondence correction unit included in the operation device of the dimension measuring apparatus.

Next, a description is given on the incorrect correspondence detecting processing in Step S501 (see FIG. 5) with reference to FIG. 6, FIG. 7, FIG. 9A, and FIG. 9B. The flowchart in FIG. 6 is drawn with one of the contour of the reference pattern and the contour of the inspection pattern denoted as "Contour A", and with the other as "Contour B". In the incorrect correspondence detecting processing in Step S501, both processings of the processing in which "the contour of the reference pattern is Contour A and the contour of the inspection pattern is Contour B" and the processing in which "the contour of the inspection pattern is Contour A and the contour of the reference pattern is Contour B" are performed.

As shown in the flowchart in FIG. 6, the correspondence correction unit 104 sets the value of a counter N to "0" in Step S601.

In Step S602, the correspondence correction unit 104 judges whether the connection destination of the N-th contour point of Contour A is valid or not. When the connection destination of the N-th contour point of Contour A is valid (YES in Step S602), the correspondence correction unit 104 proceeds to Step S605 to continue the processing. When the connection destination of the Nth contour point of Contour A is not valid (NO in Step S602), the correspondence correction unit 104 proceeds to Step S603 to continue the processing. The method for judging whether the connection destination of the N-th contour point of Contour A is valid or not is described later in detail (see FIG. 7).

In Step S603, the correspondence correction unit 104 judges whether the connection destination of the contour point of Contour B corresponding to the N-th contour point of Contour A, namely the connection destination of the contour point of Contour B that is the connection destination of the N-th contour point of Contour A is valid or not. When the connection destination of the contour point of Contour B corresponding to the Nth contour point of Contour A is not valid (NO in Step S603), the correspondence correction unit 104 proceeds to Step S605 to continue the processing. On the other hand, when the connection destination of the contour point of Contour B corresponding to the N-th contour point of Contour A is valid (YES in Step S603), the correspondence correction unit 104 marks the Nth contour point of Contour A as an incorrect correspondence in Step S604 and, after then, proceeds to Step S605 to continue the processing. The method for judging whether the connection destination of the contour point of Contour B corresponding to the N-th contour point of Contour A is valid or not is described later in detail (see FIG. 7).

In Step S605, the correspondence correction unit 104 judges whether the processing is completed for all contour points of Contour A. If there is any contour point of Contour A for which the processing is not completed (NO in Step S605), the correspondence correction unit 104 increments the value of the counter N by "unity" in Step S606 and then returns to Step S602 to continue the processing. On the other hand, if the processing is completed for all contour points of Contour A (YES in Step S605), the correspondence correction unit 104 terminates the incorrect correspondence detecting processing for Contour A. Incidentally, whether the processing is completed for all contour points of Contour A or not may be determined by comparing the value of the counter N with the total number of the contour points of Contour A.

A description is given on the operation of the correspondence correction unit 104 in the flowchart in FIG. 6 using an example in which the N-th contour point of Contour A is a contour point 902 shown in FIG. 9.

Figure 9A:
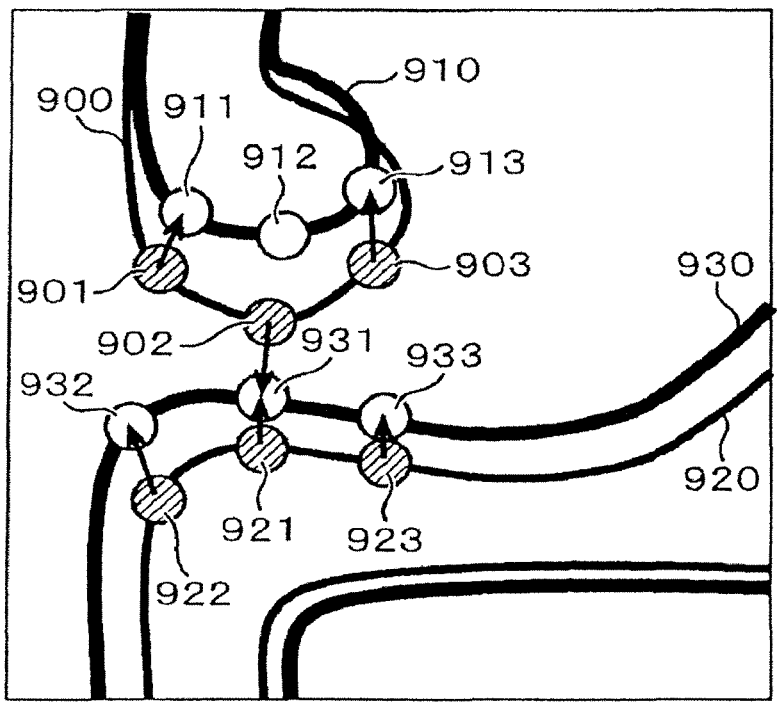
FIG. 9A and FIG. 9B are diagrams for explaining the operation in the incorrect correspondence detecting processing that is among the operations of the correspondence correction unit included in the operation device of the dimension measuring apparatus.

First, in Step S602, whether the connection destination of the contour point 902 (a first point) is valid or not is judged. Referring to FIG. 9A, the connection destination of the contour point 902 is a contour point 931 (a second point) and, referring to FIG. 9B, the connection destination of the contour point 931 is a contour point 921 (a third point). Because the contour point 902 is on a segment 900 of the reference pattern and the contour point 921 is on a segment 920 of the reference pattern, it is judged that "the connection destination of the contour point 902 is not valid" in the validity judging processing that is described later (see FIG. 7). Since it cannot be determined whether the connection destination of the contour point 902 is incorrect or the connection destination of the contour point 931 which is the connection destination of the contour point 902 is incorrect in this state, judgment of whether the connection destination of the contour point 931 is valid or not is judged is performed subsequently (Step S603).

Figure 9B:
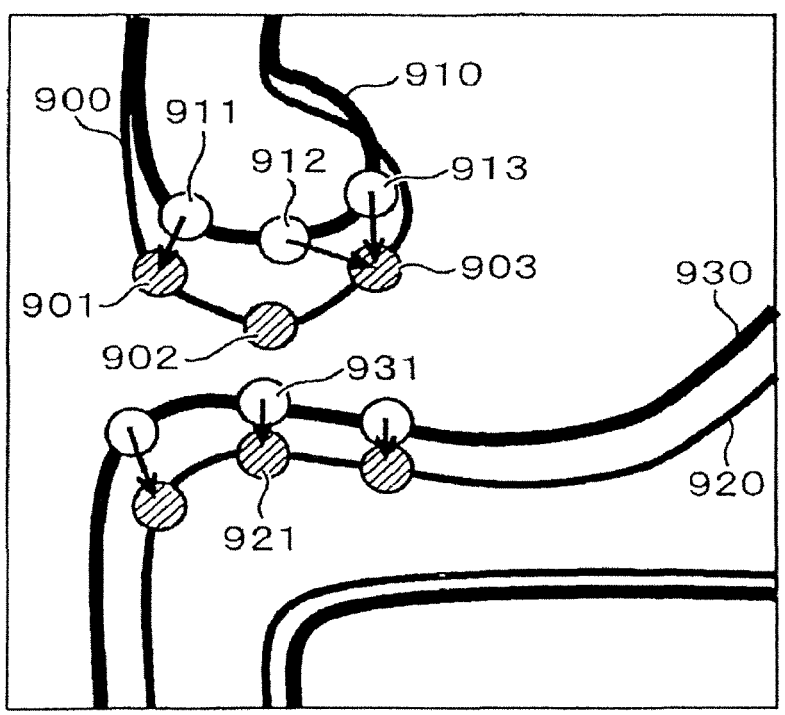

Referring to FIG. 9B, the connection destination of the contour point 931 is the contour point 921 and, referring to FIG. 9A, the connection destination of the contour point 921 is the contour point 931. Both of the contour point 931 and the contour point 931 are on the same segment 930 of the inspection pattern and, when the route between them on the segment 930 is measured, the length of the route is "0", namely they exist in the vicinity of each other; therefore, in the validity judging processing that is described later (see FIG. 7), it is judged that "the connection destination of the contour point 931 is valid". Because the possibility that "the connection destination of the contour point 931 that is the connection destination of the contour point 902 is incorrect" is denied with this, it is estimated that the cause of the judgment that "the connection destination of the contour point 902 is not valid" is that the connection destination of the contour point 902 is incorrect. Then, the contour point 902 is marked as an incorrect correspondence in Step S604.

[Validity Judging Processing]

Figure 7:
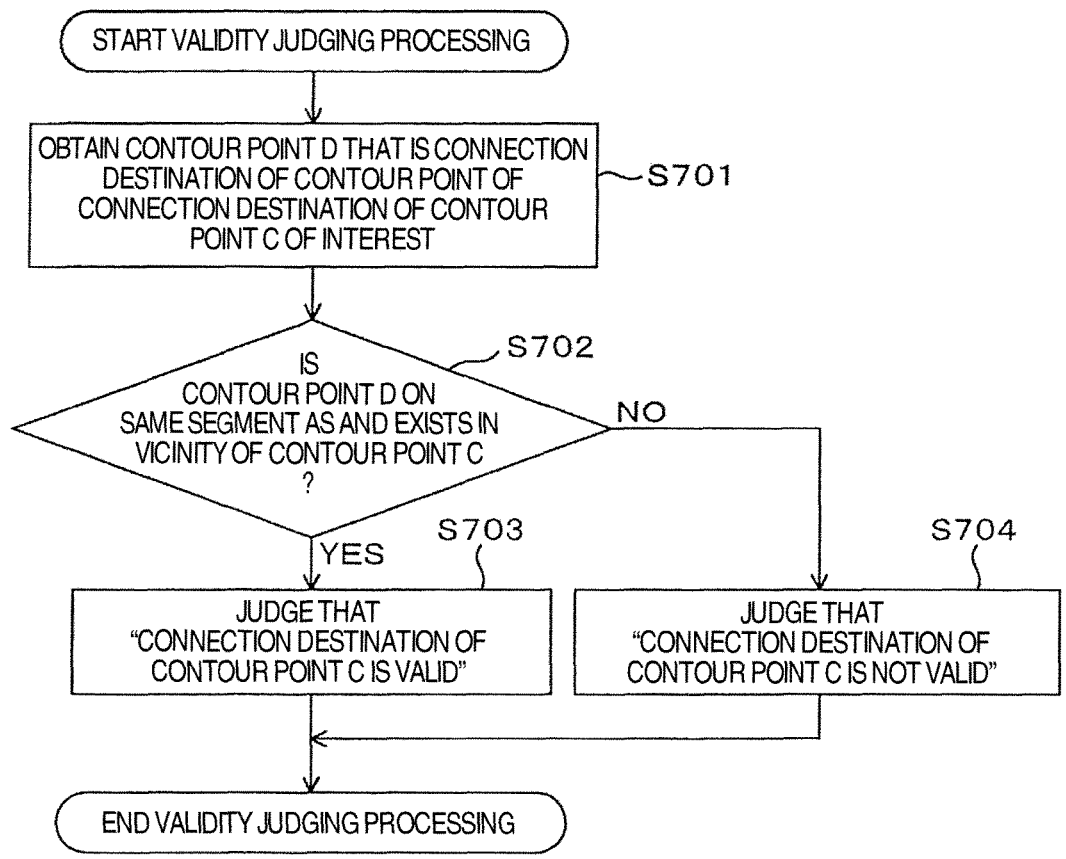
FIG. 7 is a flowchart explaining an operation in validity judging processing that is among the operations of the correspondence correction unit included in the operation device of the dimension measuring apparatus.

Next, a description is given on the validity judging processing used in Step S602 and Step S603 (see FIG. 6 for both steps) with reference to FIG. 7. As shown in the flowchart in FIG. 7, in Step S701 the correspondence correction unit 104 obtains Contour Point D that is the connection destination of the contour point of the connection destination of Contour Point C which is of interest.

Next, in Step S702, the correspondence correction unit 104 judges whether Contour Point D obtained in Step S701 is on the same segment as and exists in the vicinity of Contour Point C or not. When Contour Point D is on the same segment as and exists in the vicinity of Contour Point C (YES in Step S702), the correspondence correction unit 104 judges that "the connection destination of Contour Point C is valid" in Step S703 and, after then, terminates the validity judging processing. On the other hand, when Contour Point D is not on the same segment as Contour Point C or when it is on the same segment as but is not in the vicinity of Contour Point C (NO in Step S702), the correspondence correction unit 104 judges that "the connection destination of Contour Point C is not valid" in Step S704 and, after then, terminates the validity judging processing.

Judgment "whether it exists in the vicinity or not" in Step S702 is performed using a radius "Ra", which is defined in advance as a design value. More specifically, when Contour Point C and Contour Point D are on the segment and adjacent across contour points fewer than (Ra−1) between them (when they are in a prescribed positional relation), it judges that one "exists in the vicinity of" the other. The reason why a processing using a radius Ra is adopted in this way is because, even when the connection destination is valid, Contour Point C and Contour Point D do not strictly coincide with each other due to effects such as shapes of contours.

[Incorrect Correspondence Correcting Processing]

Next, a description is given on the incorrect correspondence correcting processing in Step S502 (see FIG. 5) with reference to FIG. 8 to FIG. 10B.

Figure 8:
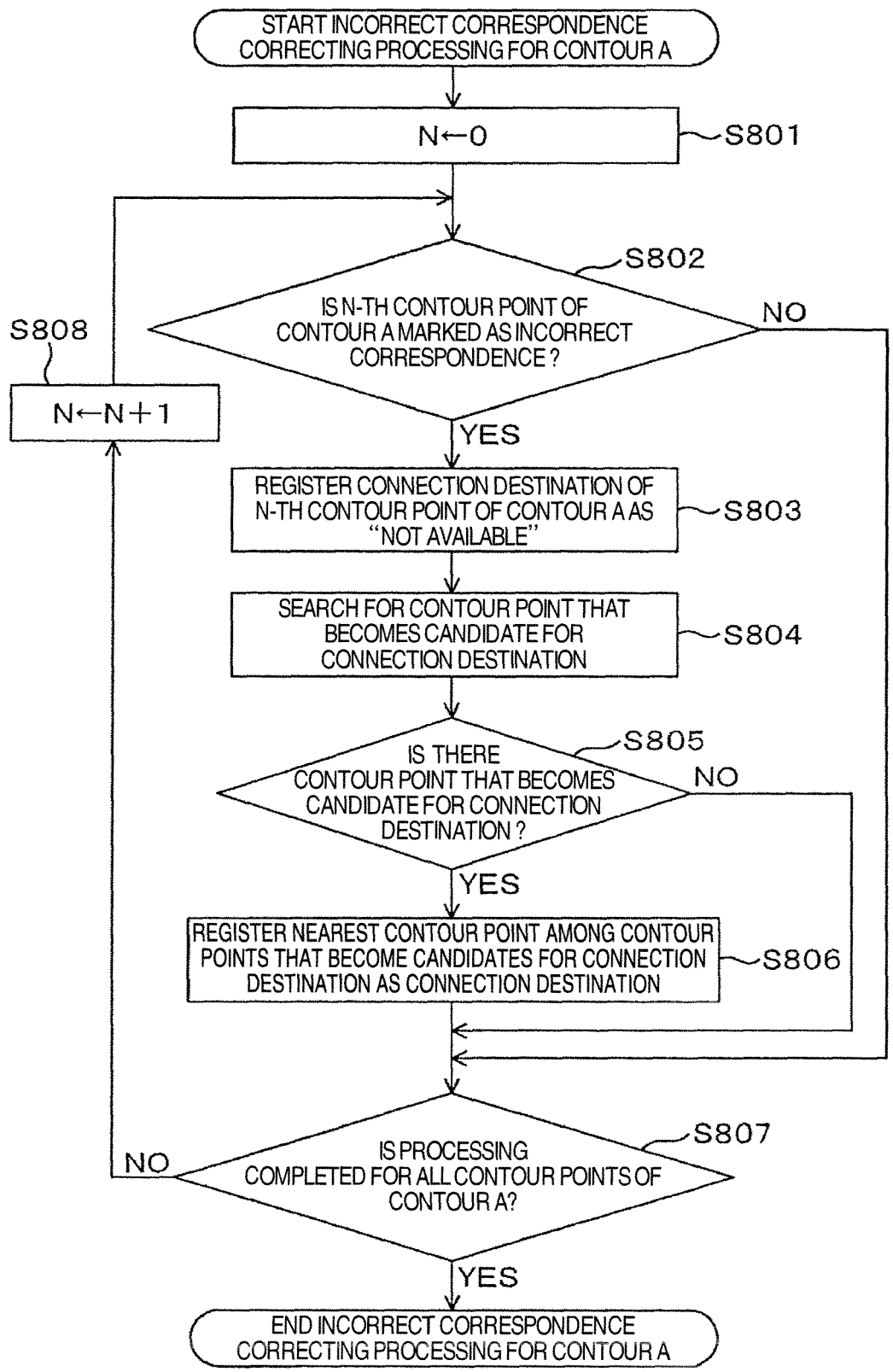
FIG. 8 is a flowchart explaining an operation in incorrect correspondence correcting processing that is among the operations of the correspondence correction unit included in the operation device of the dimension measuring apparatus.

The flowchart in FIG. 8 is drawn with one of the contour of the reference pattern and the contour of the inspection pattern denoted as "Contour A", and with the other as "Contour B". In the incorrect correspondence correcting processing in Step S502, both processings of the processing in which "the contour of the reference pattern is Contour A and the contour of the inspection pattern is Contour B" and the processing in which "the contour of the inspection pattern is Contour A and the contour of the reference pattern is Contour B" are performed.

As shown in the flowchart in FIG. 8, the correspondence correction unit 104 sets the value of a counter N to "0" in Step S801.

In Step S802, the correspondence correction unit 104 judges whether the N-th contour point of Contour A is marked as an incorrect correspondence or not. When the N-th contour point of Contour A is marked as an incorrect correspondence (YES in Step S802), the correspondence correction unit 104 registers the connection destination of the N-th contour point of Contour A as "not available" in Step S803 and, after then, proceeds to Step S804 to continue the processing. On the other hand, when the N-th contour point of Contour A is not marked as an incorrect correspondence (NO in Step S802), the correspondence correction unit 104 proceeds to Step S807 to continue the processing.

In Step S804, the correspondence correction unit 104 searches for one or more contour points that are candidates for the connection destination. More specifically, it may be performed as follows. First, on a segment which the N-th contour point of Contour A (hereinafter, referred to "Contour Point Aa") is on, contour points not marked as an incorrect correspondence are searched for along the segment shape within the range of a radius "Rb" in the forward and backward directions beginning at Contour Point Aa. Here, the value of Rb is set in advance as a design value.

(1) When contour points not marked as an incorrect correspondence are found in both the forward and backward directions, they are called Contour Point Ab and Contour Point Ac, respectively. In this case, Contour Point Bb connecting to Contour Point Ab and Contour Point Bc connecting to Contour Point Ac are obtained next. When Contour Point Bb and Contour Point Bc are on the same segment, a set of contour points existing from Contour Point Bb to Contour Point Bc on the segment becomes candidates for the connection destination of Contour Point Aa. When the segment which Contour Point Bb and Contour Point Bc are on forms a closed path, a set of contour points existing from Contour Point Bb to Contour Point Bc or a set of contour points existing from Contour Point Bc to Contour Point Bb, whichever has a smaller number of elements, is adopted to be candidates for the connection destination of Contour Point Aa. On the other hand, when Contour Point Bb and Contour Point Bc are not on the same segment, it is set that candidates for the connection destination of Contour Point Aa are "not available".

(2) When a contour point not marked as an incorrect correspondence is found only in one of the forward and backward directions, the contour point is called Contour Point Ad. In this case, Contour Point Bd connecting to Contour Point Ad is obtained next. When the segment which Contour Point Bd is on does not form a closed path and a route from Contour Point Bd to the end point nearer to Contour Point Bd (called Contour Point Be) is "Rc" or less, a set of contour points existing from Contour Point Bd to Contour Point Be becomes candidates for the connection destination of Contour Point Aa.

When the segment which Contour Point Bd is on forms a closed path or when the route from Contour Point Bd to Contour Point Be is longer than "Rc", candidates for the connection destination of Contour Point Aa are set to be "not available". Here, the value of Rc is a value defined in advance as a design value. Considering effects such as shapes of the contours, it is usually defined to satisfy "Rb≤Rc".

(3) When any contour point not marked as an incorrect correspondence is not found in either of the forward and backward directions, it is set that a contour point which becomes a candidate for a connection destination of Contour Point Aa is "not available".

In Step S805, the correspondence correction unit 104 judges whether there are contour points that become candidates for the connection destination, When there are contour points that become candidates for the connection destination (S in Step S805), the correspondence correction unit 104 proceeds to Step S806 to continue the processing. On the other hand, when there is not any contour point that becomes a candidate for the connection destination (NO in Step S805), the correspondence correction unit 104 proceeds to Step S807 to continue the processing. In this case, the connection destination of the Nth contour point of Contour A remains in the state of "not available" registered in Step S803.

In Step S806, the correspondence correction unit 104 registers a contour point which is the nearest to the N-th contour point of Contour A among the contour points becoming the candidates for the connection destination searched for in Step S804 as the connection destination of the Nth contour point of Contour A.

In Step S807, the correspondence correction unit 104 judges whether the processing is completed for all contour points of Contour A. If there is any contour point of Contour A for which the processing is not completed (NO in Step S807), the correspondence correction unit 104 increments the value of the counter N by "unity" in Step S808 and then returns to Step S802 to continue the processing. On the other hand, if the processing is completed for all contour points of Contour A (YES in Step S807), the correspondence correction unit 104 terminates the incorrect correspondence correcting processing for Contour A. Incidentally, whether the processing is completed for all contour points of Contour A or not is determined by comparing the value of the counter N with the total number of the contour points of Contour A.

The operation of the correspondence correction unit 104 in the flowchart in FIG. 8 is described using cases shown in FIG. 9A, FIG. 9B, FIG. 10A, and FIG. 10B as examples. Incidentally, in FIG. 10A and FIG. 10B, the same reference numerals as in FIG. 9A and FIG. 9B denote the same elements in FIG. 9A and FIG. 9B.

Figure 10A:
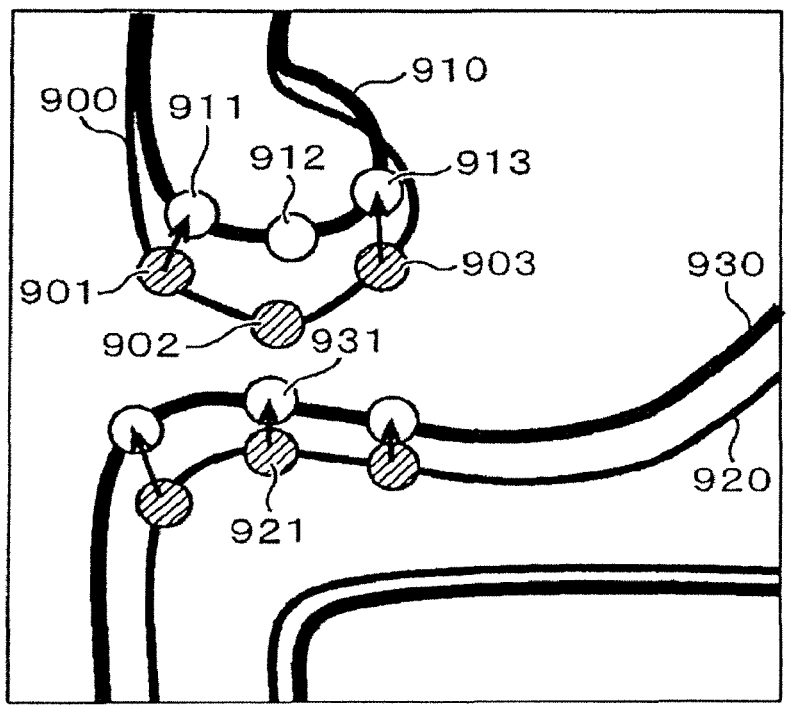
FIG. 10A and FIG. 10B are diagrams for explaining the operation in the incorrect correspondence correcting processing that is among the operations of the correspondence correction unit included in the operation device of the dimension measuring apparatus.
Figure 10B:
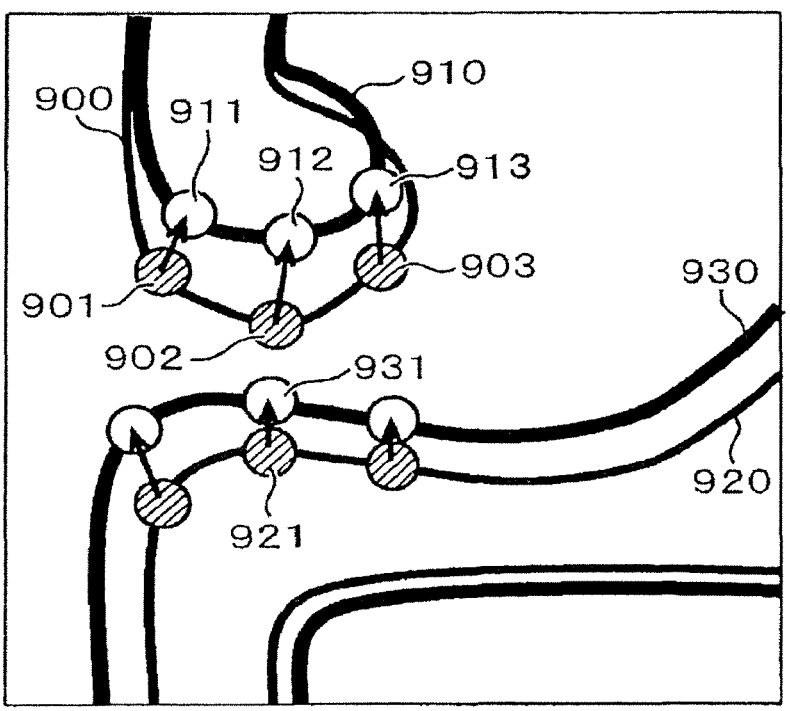

In the state of FIG. 9, the contour point marked as an incorrect correspondence, that is one for which it becomes YES in Step S802, is the contour point 902 only, and for the other contour points, the connection destinations are not corrected. The connection destination of the contour point 902 is first registered as "not available" in Step S803. This state is shown in FIG. 10A. Next, in Step S804, search for contour points that are candidates for the connection destination is performed. When following the contour points along the segment 900 in both directions beginning at the contour point 902, the contour point 901 and the contour point 903 are found in the respective directions as contour points not marked incorrect correspondences. Since the contour point 911 which is the connection destination of the contour point 901 and the contour point 913 which is the connection destination of the contour point 903 belong to the same segment 910 and, in addition, they are in the vicinity of each other with regard to the route of the segment 910, among the contour points belonging to the segment 910, contour points included in the section from the contour point 911 to the contour point 913, namely the contour point 911, the contour point 912, and the contour point 913 are selected as the candidates for the connection destination of the contour point 902. Because there are contour points that are the candidates for the connection destination, it proceeds to Step S806 in the judgment in Step S805, and in the processing in Step S806 the contour point 912 is registered, which is the nearest to the contour point 902 among the contour point 911, the contour point 912, and the contour point 913, as the connection destination of the contour point 902. As a result, the correspondence such as the one shown in FIG. 10B can be obtained.

[Operation of Inspection Unit 105 in Pattern Inspection Device 100]

Next, a description is given on the operation of the inspection unit 105 with reference to FIG. 11. The flowchart in FIG. 11 is drawn with one of the contour of the reference pattern and the contour of the inspection pattern denoted as "Contour A", and the other as "Contour B". Although Contour B is not described, it is used in Step S1104 described later in calculating an Edge Placement Error (EPE) value. In the present embodiment, the EPE value is defined as "a length of a directed line segment". The inspection unit 105 performs both processings of the processing in which "the contour of the reference pattern is Contour A and the contour of the inspection pattern is Contour B" and the processing in which "the contour of the inspection pattern is Contour A and the contour of the reference pattern is Contour B".

As shown in the flowchart in FIG. 11, the inspection unit 105 sets the value of a counter N to "0" in Step S1101.

In Step S1102, the inspection unit 105 judges whether there is the connection destination of the N-th contour point of contour A or not. When there is the connection destination of the N-th contour point of Contour A (YES in Step S1102), the inspection unit 105 proceeds to Step S1104 to continue the processing. On the other hand, when there is not the connection destination of the N-th contour point of Contour A (NO in Step S 1102), the inspection unit 105 marks the N-th contour point of Contour A as a defect in Step S1103 and, after then, proceeds to Step S1106 to continue the processing.

In Step S1104, the inspection unit 105 calculates the EPE value of the N-th contour point of Contour A and judges whether the calculated EPE value is equal to or less than a threshold. When the EPE value of the N-th contour point of Contour A is equal to or less than the threshold (YES in Step S1104), the inspection unit 105 proceeds to Step S1106 to continue the processing. On the other hand, when the EPE value of the N-th contour point of Contour A is greater than the threshold (NO in Step S1104), the inspection unit 105 marks both the N-th contour point of Contour A and the contour point of the connection destination of the N-th contour point of Contour A as defects in Step S1105 and, after then, proceeds to Step S1106 to continue the processing.

In Step S1106, the inspection unit 105 judges whether the processing is completed for all contour points of Contour A. If there is any contour point of Contour A for which the processing is not completed (NO in Step S1106), the inspection unit 105 increments the value of the counter N by "unity" in Step S1107 and then returns to Step S1102 to continue the processing. On the other hand, if the processing is completed for all contour points of Contour A (YES in Step S1106), the inspection unit 105 outputs information about the contour points marked as defects and terminates the inspection processing for Contour A. Whether the processing is completed for all contour points of Contour A or not may be determined by comparing the value of the counter N with the total number of the contour points of Contour A.

As the above-mentioned, according to the first embodiment, with regard to respective correspondences included in the correspondence information generated in the correspondence generation unit, the consistency is judged using information on a vicinity area of a point on the reference pattern along the contour of the reference pattern and information on a vicinity area of a point on the inspection pattern along the contour of the inspection pattern in the correspondence, and inconsistent correspondences, if any, are corrected before being used in the inspection, then, the frequency at which incorrect correspondences between the points on the contour of the reference pattern and the points on the contour of the inspection pattern are used in the inspection can be reduced, thus improving reliability in the inspection results.

Figure 13:
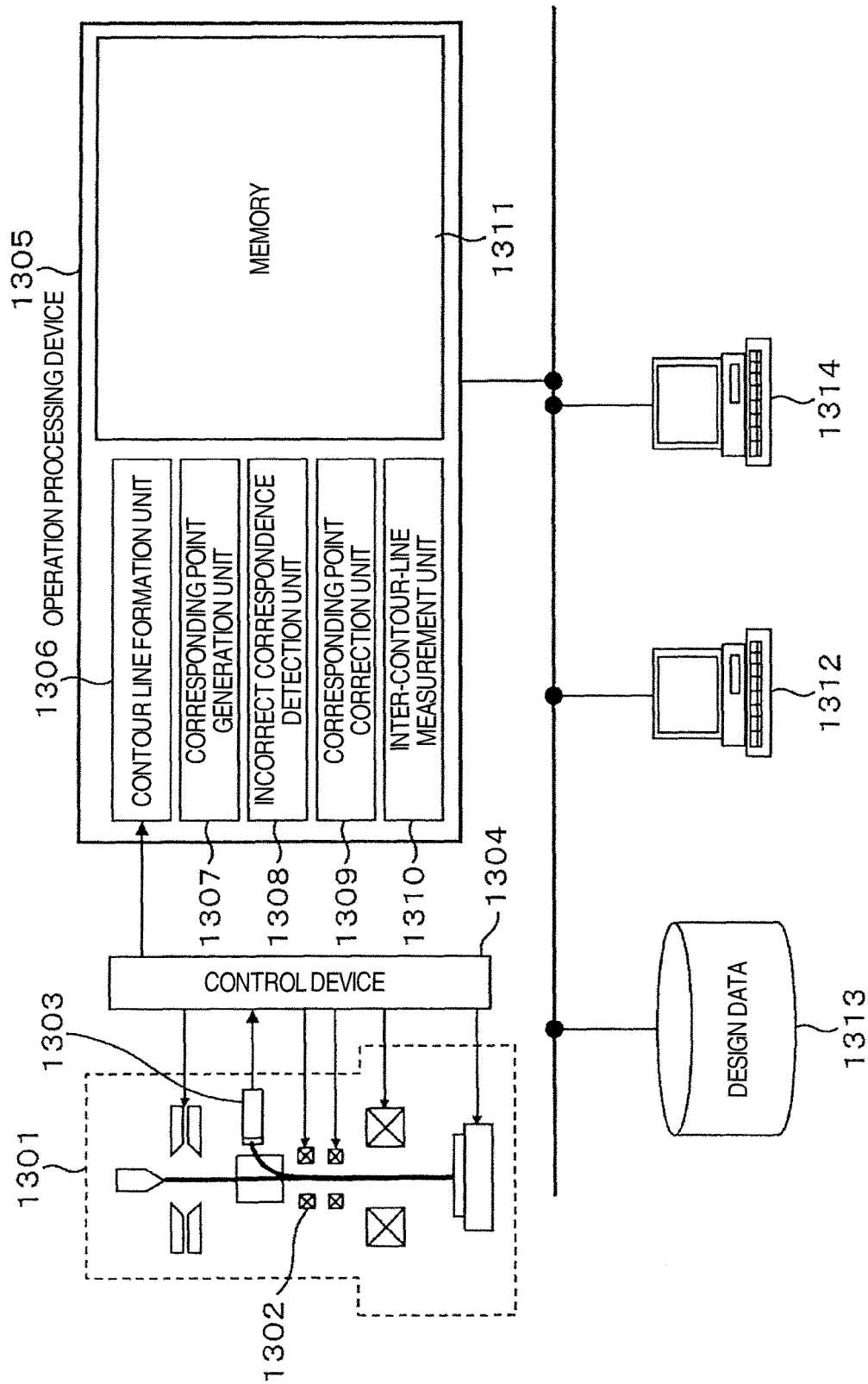
FIG. 13 is a diagram showing an example of the dimension measuring apparatus that includes a scanning electron microscope.

FIG. 13 is a diagram showing an example of a dimension measuring apparatus having a scanning electron microscope (SEM) as the image-capturing device. Incidentally, although an example in which an SEM is used as the image-capturing device is described in the present embodiment, it is not limited thereto, for example, a focused ion beam device, which forms a scanned image based on a signal obtained by scanning a sample with a focused ion beam, may also be adopted as the image-capturing device.

A body of an SEM 1301, a control device 1304 of the body of the SEM, and an operation processing device 1305 are included. The operation processing device 1305 functions as an image processing device that forms a contour line from an obtained image. The control device 1304 enables beam scanning under desired conditions by controlling the body of the SEM 1301. The control device 1304 supplies a deflection signal to set a scan position at a desired location on a sample to a deflector 1302. The deflector 1302 changes the size of the field of view (the magnification) to a desired size according to the supplied signal. The control device 1304 performs image processing on an image that is obtained by arranging detected signals obtained by a detector 1303 in synchronization with scanning of the deflector 1302.

In the operation processing device 1305, a contour line formation unit 1306 that generates contour line data based on the obtained image signal, a corresponding point generation unit 1307 that executes the processings such as S203 in FIG. 2, an incorrect correspondence detection unit 1308 that executes the processings such as S501 in FIG. 5, a corresponding point correction unit 1309 that executes the processings such as S502 in FIG. 5, and an inter-contour-line measurement unit 1310 that measures a distance between corresponding points are included. Further, information necessary for processings executed in the operation processing device 1305 is stored in a memory 1311 in the operation processing device 1305 as a measurement recipe. A recipe is an operation program for causing the SEM to operate automatically, and is stored in the memory 1311 or an external storage medium and read as needed for each type of samples to be measured.

Electrons emitted from a sample are captured at the detector 1303 and are converted to a digital signal with an A/D converter built in the control device 1304. Image processing is performed with image processing hardware such as a CPU, an ASIC, and an FPGA which are built in the operation processing device 1305, according to a purpose. The operation processing device 1305 also has a function to create a line profile based on the detection signal.

In addition, the operation processing device 1305 is connected to an input device 1312 that has an input means and has a function such as a graphical user interface (GUI) via which an image or inspection results are displayed to an operator with a display device provided to the input device 1312.

It is also possible to assign part or all of the control and/or the processings in the operation processing device 1305 to an electronic computer that has a CPU and/or a memory in which images can be accumulated or the like to perform processings and control. Furthermore, the input device 1312 also functions as an image-capturing recipe creation device that creates an image-capturing recipe, which includes a position of an electronic device required for measurement, inspection, or the like, a template for pattern matching used for positioning, image-capturing conditions, and the like, either manually or utilizing design data stored in a storage medium 1313 of an electronic device design data. In a simulator 1314 a simulation is performed on a pattern shape based on design data stored in a design data storage medium 1313 Data of the reference pattern described above may be generated based on such a simulation.

Second Embodiment

Hereinafter, a description is given on a second embodiment. A pattern inspection device of the present embodiment is different from the pattern inspection device 100 of the first embodiment only in that it includes a correspondence correction unit 104A instead of the correspondence correction unit 104. Because an operation of the correspondence correction unit 104A is different from the operation of the correspondence correction unit 104 only in the validity judging processing, the following describes only the validity judging processing with reference to FIG. 9 and FIG. 12. The other configuration is the same as that of the first embodiment and, therefore, the description is omitted.

[Validity Judging Processing]

Figure 12:
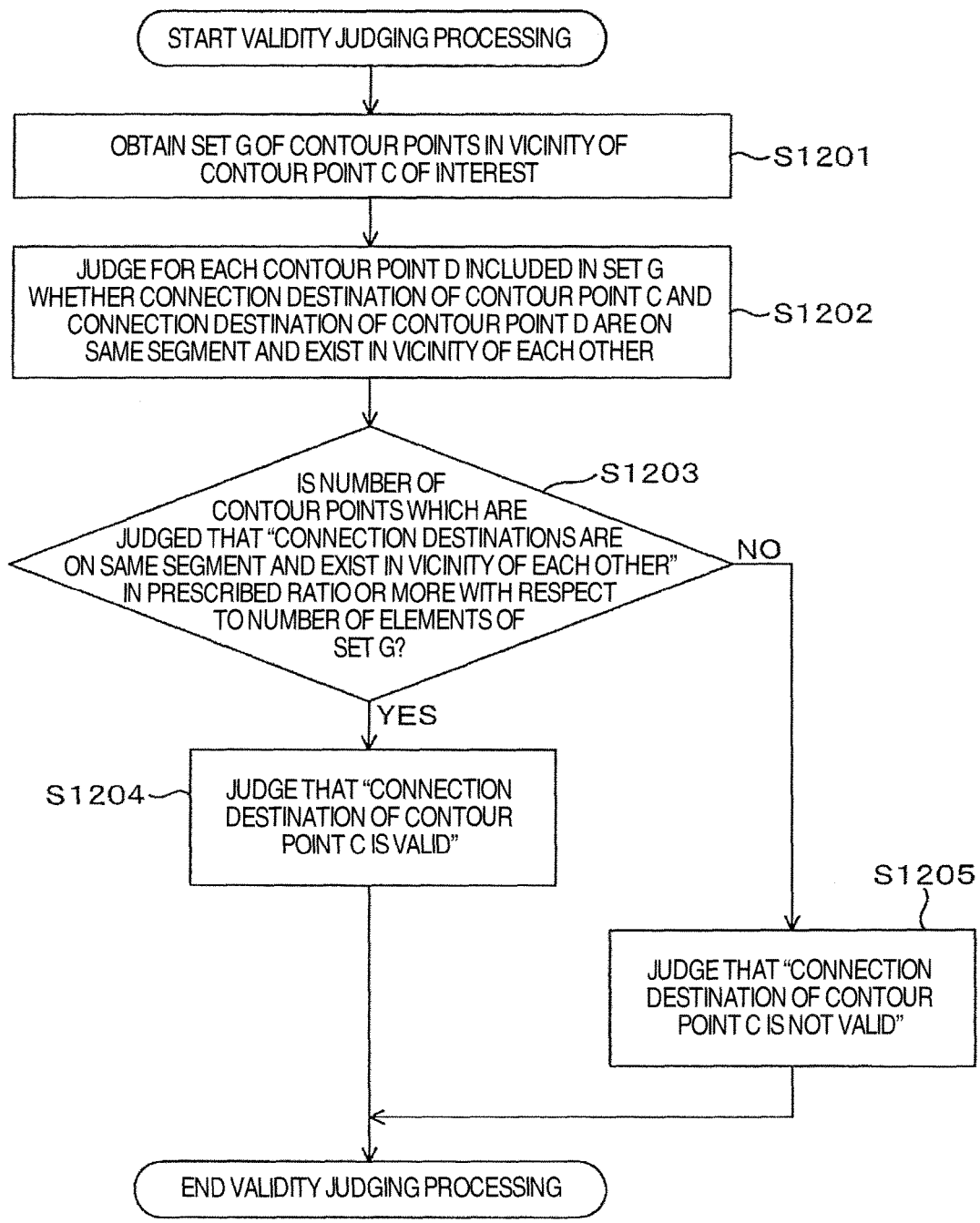
FIG. 12 is a flowchart explaining another operation in validity judging processing that is among the operations of the correspondence correction unit included in the operation device of the dimension measuring apparatus.

As shown in the flowchart in FIG. 12, in Step S1201, the correspondence correction unit 104A obtains a set G of contour points in the vicinity of Contour Point C which is of interest. More specifically, the set G is rendered to be a set of Rd contour points in front and behind of Contour Point C, respectively, on the segment which Contour Point C is on, not including Contour Point C. Incidentally, when the segment which Contour Point C is on forms a closed path, the set G is created so that duplicate elements are not included. If Contour Point C exists in the vicinity of an end of a segment and Rd elements cannot be selected, the contour points to the end are included in the set G. It is noted that the radius "Rd" is a value defined in advance as a design value.

Next, in Step S1202, the correspondence correction unit 104A judges, for each Contour Point D included in the set G, whether the connection destination of Contour Point C and the connection destination of Contour Point D are on the same segment and exist in the vicinity of each other, and counts the number of contour points each of which is judged that "the connection destination is on the same segment as and exists in the vicinity of the connection destination of Contour Point C".

The judgment whether the connection destination of Contour Point C and the connection destination of Contour Point D are on the same segment and exist in the vicinity of each other is the same as in Step S702 (see FIG. 7) except that the radius used for the definition of "the vicinity" is "Re" and, therefore, the description is omitted. Incidentally, the radius "Re" is a value defined in advance as a design value. Because it is affected by shape of contours, it is usually defined to satisfy "Rd Re" in consideration of a margin for the effect.

Next, in Step S1203, the correspondence correction unit 104A judges whether the number of the contour points which are judged in Step S1202 that "the connection destinations are on the same segment and exist in the vicinity of each other" is in a prescribed ratio or more with respect to the number or the elements of the set G When it is judged that "it is in the prescribed ratio or more" (YES in Step S1203), the correspondence correction unit 104A judges in Step S1204 that "the connection destination of Contour Point C is valid" and terminates the validity judging processing. On the other hand, when it is judged that "it is not in the prescribed ratio or more" (NO in Step S1203), the correspondence correction unit 104A judges in Step S1205 that "the connection destination of Contour Point C is not valid" and terminates the validity judging processing. Incidentally, for the "prescribed ratio" used in the judgment in Step S1203, a value defined in advance as a design value is used.

Hereinafter, referring to FIG. 9A, the judging processing in Step S1203 for each of the contour point 902 and the contour point 921 is described where "Rc=1", "Rd=1", and "the prescribed ratio" is "0.5".

With regard to the contour point 902, first, in Step S1201, a set G composed of the contour point 901 and the contour point 903 is generated. Next, in Step S1202, the number of the contour points that are judged that "the connection destinations are on the same segment as and exist in the vicinity of the connection destination of the contour point 902" is counted. While the connection destination of the contour point 902 is the contour point 931 on the segment 930, the connection destination of the contour point 901 is the contour point 911 on the segment 910 and the connection destination of the contour point 903 is the contour point 913 on the segment 910; therefore, the number of the contour points that are judged "the connection destinations are on the same segment as and exist in the vicinity of the connection destination of the contour point 902" is "0". Because the number of the elements of the set G is "2" and the "prescribed ratio" is "0.5", the judgment in Step S1203 becomes "NO" and, in Step S1205, it is judged that "the connection destination of the contour point 902 is not valid".

With regard to the contour point 921, first, in Step S1201, a set G composed of the contour point 922 and the contour point 923 is generated. Next, in Step S1202, the number of the contour points that are judged that "the connection destinations are on the same segment as and exist in the vicinity of the connection destination of the contour point 921" is counted. While the connection destination of the contour point 921 is the contour point 931 on the segment 930, the connection destination of the contour point 922 is the contour point 932 on the segment 930 and the connection destination of the contour point 923 is the contour point 933 on the segment 930; therefore, the number of the contour points that are judged "the connection destinations are on the same segment as and exist in the vicinity of the connection destination of the contour point 921" is "2". Because the number of the elements of the set G is "2" and the "prescribed ratio" is "0.5", the judgment in Step S1203 is "YES" and, in Step S1204, it is judged that "the connection destination of the contour point 921 is valid".

As the above-mentioned, according to the second embodiment, even when a correspondence of contour points can not be defined by a directed line segment, that is even when the information shown in FIG. 9B is not given, the validity of the correspondence can be judged in light of the surrounding conditions and an incorrect correspondence can be corrected. In addition, according to the present embodiment, even if a pair of incorrect correspondences is generated by accident between a point on a contour of a reference pattern and a point on a contour of an inspection pattern, the incorrect correspondences can be detected and corrected.

<Modifications>

Although two embodiments are described up to this point, it is not limited thereto and the following modifications may be made without departing from the spirit described above.

Although a correspondence of contour points can be represented with a directed line segment in the embodiments described above, the present embodiments are not limited thereto. For example, it is applicable also to the case in which, for a point H on a contour of a reference pattern, a corresponding point is searched for in a direction perpendicular to a tangent line to the reference pattern at the point H and an obtained point on an inspection pattern is used as the point corresponding to the point H. In such a case, the second embodiment, in which a correspondence from a point on the contour of the inspection pattern to a point on the contour of the reference pattern is not necessary, is preferable.

Also, although a contour obtained from an inspection image is resolved into segments and converted to contour points to use in the embodiments described above, present embodiments are not limited thereto. For example, a contour obtained from an inspection mage may be resolved into segments and, after geometric smoothing is applied, contour points may be set to use. By adopting processing in this way, the effect of noises can be reduced. Incidentally, in this case, a smoothing processing in which a position of an end point shared by a plurality of segments won't change may be adopted or processing in which the result of a change in the position of an end point is reflected on all related segments would be adopted Further, although the "vicinity" is defined on a segment basis in the embodiments described above, the present embodiments are not limited thereto. For example, by storing the information about "which segment an end point is shared with" on a segment basis, a range of the "vicinity" may be changed to include segments that share the end point. Such a change is easy to implement.

Moreover, although the "vicinity" is defined using "the number of contour points" on each segment in the embodiments described above, the present embodiments are not limited thereto. For example, it may be changed to a definition using a "route" on each segment and such a change is easy to implement.

Furthermore, although in the embodiments described above it is configured in a way such that contour points generated in prior to being associated are associated with each other for both of a contour of a reference pattern and a contour of an inspection pattern, the present embodiments are not limited thereto. Namely, representation methods of a contour of a reference pattern and a contour of an inspection pattern are not limited to sets of contour points, or it is not limited to the case where points generated in advance for both a contour of a reference pattern and a contour of an inspection pattern are associated with each other. For example, for a case in which a configuration is adopted such that a point on a contour of an inspection pattern corresponding to a given point on a contour of a reference pattern is obtained each time based on the point on the contour of the reference pattern, for example, instead of by resolving the contour of the inspection pattern into segments and performing the contour point setting processing with an even spacing, but by performing the processing of the correspondence correction unit using corresponding points obtained based on the points on the contour of the reference pattern as the contour points, the first embodiment may be applied. In that case, regarding the definition of the "vicinity", it is preferable that it is defined by a "route" on a segment, not by the "number of contour points" on a segment.

Also, although the correspondences between the contour points are generated based only on the distances in the embodiments described above, the present embodiments are not limited thereto. For example, the correspondences between the contour points may be generated considering not only the distances but also angles of tangential line directions. More specifically, for example, only contour points having approximately the same tangential line directions are selected as the candidates for the connection destination and the contour point of the shortest distance may be associated among the selected candidates. Alternatively, the correspondence may be made based on an evaluation value which is obtained by adding up an absolute value of a difference in the angles of the tangential line directions and the distance multiplied by prescribed weights, respectively.

Further, although the inspection unit 105 is configured in such a way that the information on a contour point marked as a defect is output as is in the embodiments described above, the present embodiments are not limited thereto. For example, it may be configured that contour points, which are close to each other on an inspection image, are collected as one group out of contour points marked as defects and recognized as a "defective area" and the defective area is output. Such a change may be implemented easily by combining known technologies such as morphological operation, resolving of connection components with labeling, and so on, for example.

Moreover, although the purpose of the processing of the inspection unit is to "extract a part estimated to be a defect" in the embodiments described above, the present embodiments are not limited thereto. For example, it is applicable to an application such as shape evaluation in which the result of a pattern on a wafer is evaluated using a statistic obtained from the EPE values of individual contour points. It is also applicable to the case in which, for a pair of a reference pattern and an inspection pattern for which approximate positioning has been performed, more accurate positioning is performed using the information on the respective contours as a pre-process of inspection performed in the inspection unit.

Furthermore, although an inspection image is supplied from the image-capturing device 110 in the embodiments described above, the present embodiments are not limited thereto. For example, it may be configured such that an inspection image transmitted via a network or the like is received and inspected, or may be configured such that an inspection image is read from a storage medium in which the inspection image is stored and is inspected. Such a change may be easily implemented simply by properly changing an interface of the part through which an inspection image is received.

Also, although the inspection result is output to the display device 130 in the embodiments described above, the present embodiments are not limited thereto. For example, it may be configured such that the inspection result is output to another device via a network or the like; or may be configured such that the inspection result is written into a storage medium for storing the inspection result. Such a change may be easily implemented simply by properly changing an interface of the part through which the inspection result is output.

Further, although as a reference pattern one approximating a curve which forms an outer shape of an exposure pattern obtained by a lithography simulator with a polygon is used in the embodiments described above, the present embodiments are not limited thereto Various modifications are possible such as, for example, a design data representing a pattern to be formed on a wafer, a design data with corner portions thereof rounded so that it becomes close to a pattern to be formed on a wafer in reality, a contour extracted from an image of a product pattern judged to be good, and the like.

Moreover, although it is so configured that the correspondence generation unit performs the segment resolving processing and the contour point setting processing for the reference pattern in the embodiments described above, the present embodiments are not limited thereto; instead, the segment resolving processing and the contour point setting processing may be performed in advance. In that case, the contour point setting processing should be conducted using parameters with which contour points are obtained at dense enough intervals in consideration of a margin accompanied by correction performed in the coordinate correction unit.

Furthermore, although calculation of the EPE value is carried out in the inspection unit in the embodiments described above, the present embodiments are not limited thereto. For example, it may be calculated in the correspondence generation unit and the correspondence correction unit every time the connection destination of each contour point is registered.

Also, although the correspondence correction unit performs its operation to select a connection destination of a contour point marked as an incorrect correspondence from contour points which are candidates for the connection destination and then to correct in the embodiments described above, the present embodiments are not limited thereto. For example, when it is applied to a case where the purpose is accomplished simply by correcting a connection destination of a contour point marked as an incorrect correspondence to "not available", the processing of searching for a contour point that is a candidate for the connection destination or of selecting an appropriate contour point from contour points that are candidates for the connection destination may be omitted.

As the above-mentioned, according to the embodiments described above, by adopting a configuration with which, regarding a correspondence obtained from local information, consistency is judged based on the surrounding conditions and a correspondence which is estimated inconsistent is corrected to use in inspection, a frequency at which an incorrect correspondence between a point on a contour of a reference pattern and a point on a contour of an inspection pattern is used in the inspection can be reduced, thus improving reliability of the inspection result.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. An apparatus for detecting a defect in a wafer pattern based on a comparison between a first point of a first data contour and a second point of a second data contour, the first data contour being a reference pattern, the second data contour being a pattern to be evaluated, the apparatus comprising:
an image capturing device configured to capture image data corresponding to the pattern to be evaluated;
a processing system comprising a processor and control code programmed to receive the image data from the image capturing device;
generate the second data contour by extracting data points corresponding to an edge of the pattern from the image data, the second data contour including a plurality of segments configuring a pattern, each of the plurality of segments including a plurality of the data points, the second point being one of the plurality of data points;
associate the first point and the second point with each other when a distance between the first point and the second point satisfies a condition;
determine whether the second point is also selected to be associated with a third point on the first data contour;
correct the association of the first point with the second point when it is determined that the second point is also selected to be associated with the third point; and
output whether the wafer pattern includes the defect based on the comparison between the first and second data contours,
wherein the first data contour is divided into a plurality of segments configuring a patter,
wherein the comparison between the first and second data contours is based on an inspection of the plurality of points of the second data contour,
wherein the inspection of the plurality of points of the second data contour includes:
determining there is a defect when a point of the second data contour does not correspond to a point of the first data contour,
calculating an edge placement error value for a point of the second data contour when the point of the second data contour corresponds to a point of the first data contour; and
determining there is a defect when the edge placement error value is greater than a threshold.

2. The apparatus according to claim 1 wherein the processing system judges whether the first point and the third point are in a prescribed positional relation or not.

3. The apparatus according to claim 1 wherein, when the first point and the third point are not on a same segment, the processing system searches for an other corresponding point that corresponds to the first point, with respect to the second data contour.

4. The apparatus according to claim 3 wherein the processing system searches for candidates for the other corresponding point from information on points on the second data contour that correspond to other points belonging to a same segment to which the first point belongs, and selects a point nearest to the first point from candidates searched for as a point corresponding to the first point.

5. The apparatus according to claim 1 wherein, when the segment to which the first point belongs and the segment to which the third point belongs are judged to be same, the processing system measures a dimension between the first point and the second point.

6. The apparatus according to claim 1 wherein the processing system divides the data contour on a branching point basis.

7. A computer-readable medium comprising a computer program which causes a computer to detect a defect in a wafer pattern based on a comparison of a first data contour and a second data contour, the first data contour being a reference pattern, the second data contour being the pattern to be evaluated, wherein the program causes the computer to
receive image data from an image capturing device;
generate the second data contour, by extracting data points corresponding to an edge of the pattern from the image data, the second data contour including a plurality of segments configuring a pattern, each of the plurality of segments including a plurality of the data points, the second point being one of the plurality of the data points;
associate the first point and the second point with each other when a distance between the first point and the second point satisfies a condition;
determine whether the second point is also selected to be associated with a third point on the first data contour;
correct the association of the first point with the second point when it is determined that the second point is also selected to be associated with the third point, and
output whether the wafer pattern includes the defect based on a comparison between the first and second data contours,
wherein the first data contour is divided into a plurality of segments configuring a pattern,
wherein the comparison between the first and second data contours is based on an inspection of the plurality of points of the second data contour,
wherein the inspection of the plurality of points of the second data contour includes:
determining there is a defect when a point of the second data contour does not correspond to a point of the first data contour, calculating an edge placement error value for a point of the second data contour when the point of the second data contour corresponds to a point of the first data contour; and determining there is a defect when the edge placement error value is greater than a threshold.

8. The computer-readable medium according to claim 7 wherein the program causes the computer to judge whether the first point and the third point are in a prescribed positional relation or not.

9. The computer-readable medium according to claim 7 wherein, when the segment to which the first point belongs and the segment to which the third point belongs are judged to be same, the program causes the computer to measure a dimension between the first point and the second point.

* * * * *